(12) United States Patent
Texier et al.

(10) Patent No.: US 10,711,201 B2
(45) Date of Patent: Jul. 14, 2020

(54) METHOD FOR CONVERTING ALGAL BIOMASS INTO A GAS OR INTO BIOCRUDE BY HYDROTHERMAL GASIFICATION OR HYDROTHERMAL LIQUEFACTION, RESPECTIVELY

(71) Applicant: COMMISSARIAT A L'ENERGIE ATOMIQUE ET AUX ENERGIES ALTERNATIVES, Paris (FR)

(72) Inventors: Jonathan Texier, Nieul le Virouil (FR); Pierre Castelli, Saint-Nazaire les Ezymes (FR); Anne Roubaud, Chabons (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/537,329

(22) PCT Filed: Dec. 21, 2015

(86) PCT No.: PCT/EP2015/080854
§ 371 (c)(1),
(2) Date: Jun. 16, 2017

(87) PCT Pub. No.: WO2016/097414
PCT Pub. Date: Jun. 23, 2016

(65) Prior Publication Data
US 2017/0342327 A1 Nov. 30, 2017

(30) Foreign Application Priority Data
Dec. 19, 2014 (FR) ..................... 14 63026

(51) Int. Cl.
*C10G 1/06* (2006.01)
*C10G 3/00* (2006.01)
*C10J 3/82* (2006.01)
*C12P 7/00* (2006.01)

(52) U.S. Cl.
CPC ............... *C10G 1/06* (2013.01); *C10G 3/40* (2013.01); *C10J 3/82* (2013.01); *C12P 7/00* (2013.01); *C10G 2300/1014* (2013.01); *C10J 2300/0916* (2013.01); *Y02E 50/343* (2013.01); *Y02P 30/20* (2015.11); *Y02W 10/37* (2015.05)

(58) Field of Classification Search
CPC ...... C10G 1/06; C10G 300/1014; C10G 3/40; C10J 2300/091; C10J 3/82; C12P 7/00; Y02E 50/343; Y02E 30/20; Y02W 10/37
See application file for complete search history.

(56) References Cited

U.S. PATENT DOCUMENTS

| | | | | |
|---|---|---|---|---|
| 4,338,199 A * | 7/1982 | Modell | ...................... | C02F 1/00 210/721 |
| 4,428,828 A * | 1/1984 | Bose | ...................... | C10G 27/06 208/130 |
| 5,106,513 A | 4/1992 | Hong | | |
| 5,250,193 A * | 10/1993 | Sawicki | ............... | C02F 11/08 210/758 |
| 6,093,311 A * | 7/2000 | Blum | ...................... | C10G 17/00 208/251 R |
| 6,709,602 B2 * | 3/2004 | Spritzer | ...................... | B09B 3/00 210/750 |
| 8,961,794 B2 * | 2/2015 | Fjare | ...................... | C10G 1/02 210/634 |
| 2010/0064573 A1 * | 3/2010 | Brenes | ............... | C01B 13/0259 44/308 |
| 2012/0055077 A1 | 3/2012 | Savage et al. | | |
| 2012/0210632 A1 * | 8/2012 | Hong | ...................... | C10G 1/047 44/307 |
| 2012/0285077 A1 | 11/2012 | Oyler | | |
| 2013/0331623 A1 * | 12/2013 | Elliott | ...................... | C10L 3/08 585/240 |
| 2014/0273141 A1 | 9/2014 | Atwood | | |

FOREIGN PATENT DOCUMENTS

WO    2011049572 A1    4/2011

OTHER PUBLICATIONS

Pham et al. Bioresource Technol. (2013) 149: 136-135 (Year: 2013).*
International Search Report received in connection with international application No. PCT/EP2015/080854; dated Mar. 18, 2016.
Preliminary Search Report received in connection with French Application No. FR14 63026; dated Oct. 14, 2015.
Faeth, et al., "Fast Hydrothermal Liquefaction of *Nannochloropsis* sp. to Produce Biocrude", Energy Fuels, 27(3), pp. 1391-1398, (2013).
Lam, et al., "Microalgae biofuels: A critical review of issues, problems and the way forward", Biotechnology Advances, vol. 30, pp. 673-690, (2012).
Milledge, et al., "Methods of energy extraction from microalgal biomass: a review", Reviews in Environmental Science and Bio-Technology, vol. 13(3), pp. 301-320, (2014).
Pruvost, et al., "Industrial production of microalgae and cyanobacteria" Techniques de l'ingenieur, IN 200, V1, pp. 1-22, (Nov. 10, 2011).
Stucki, et al., "Catalytic gasification of algae in supercritical water for biofuel production and carbon capture", Energy & Environmental Sciences, 2(5), pp. 535-541, (2009).
Zhou, et al., "A synergistic combination of algal wastewater treatment and hydrothermal biofuel production maximized by nutrient and carbon recycling", Energy & Environmental Sciences, pp. 3765-3779, (2013).

* cited by examiner

*Primary Examiner* — Susan M Hanley
(74) *Attorney, Agent, or Firm* — The Marbury Law Group, PLLC

(57) ABSTRACT

The invention relates to methods for converting algal biomass into a gas or into biocrude comprising (a) gasification or hydrothermal liquefaction of an algal biomass in at least one first reactor, (b) separation of the gas or biocrude produced thereby from the aqueous effluents and the $CO_2$ produced, at the outlet of the first reactor, (c) recovery of the aqueous effluents, and (d) oxidation of the aqueous effluents in at least one second reactor. Continuous processes for culture of algal biomass and conversion of the algal biomass cultivated into a gas or into a biocrude are also disclosed.

20 Claims, 3 Drawing Sheets

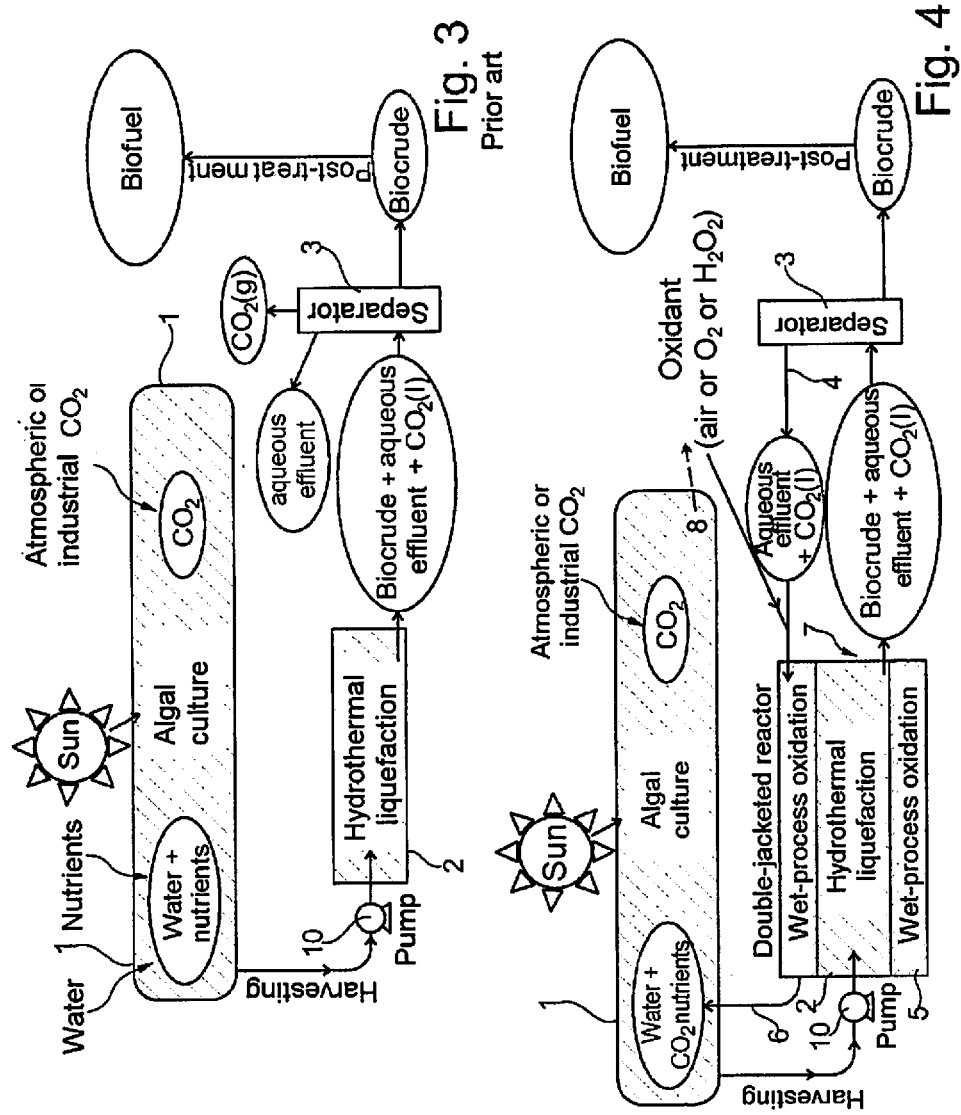

METHOD FOR CONVERTING ALGAL BIOMASS INTO A GAS OR INTO BIOCRUDE BY HYDROTHERMAL GASIFICATION OR HYDROTHERMAL LIQUEFACTION, RESPECTIVELY

CROSS REFERENCE TO RELATED APPLICATION

This is a national stage application of PCT/EP2015/080854, filed internationally on Dec. 21, 2015, which claims priority to French Application No. 1463026, filed on Dec. 19, 2014, which applications are incorporated by reference herein in their entireties.

TECHNICAL FIELD

The present invention relates to an improved method of thermochemical conversion of algal biomass, advantageously integrated continuously in a method for algal culture.

The invention aims to improve the conversion of algal biomass into a gas or into biocrude by hydrothermal gasification or hydrothermal liquefaction respectively, with a view to producing biofuels (liquid or gaseous).

"Biocrude" is intended to have its usual meaning, i.e. a combustible liquid resulting from the direct hydrothermal liquefaction of algal biomass.

"Algal biomass" means the set of the photosynthetic microorganisms.

"Photosynthetic microorganisms" is intended to have its usual meaning, as given in publication [1], namely algae and cyanobacteria, i.e. eukaryotic or prokaryotic organisms whose growth mainly takes place by photosynthesis, and of microscopic size, typically between 1 and 100 μm.

"Supercritical water" is intended to have its usual meaning, i.e. water at temperatures above 374° C. at a pressure above 22.1 MPa.

PRIOR ART

In the natural state, the photosynthetic microorganisms (microalgae and cyanobacteria) are unicellular photosynthetic organisms, the principal components of phytoplankton, which have inhabited the oceans and watercourses for more than three and a half billion years.

There has recently been an upsurge of interest in the culture of microalgae and cyanobacteria on an industrial scale because of the numerous fields of application, which include, on a decreasing scale of added value: pharmaceuticals and cosmetics, animal feed, human food, fertilizers, biosourced materials, bioremediation and biofuels (liquid or gaseous).

The upsurge of interest in this dedicated culture arises essentially because it does not have an adverse effect on food production, and because its yield, i.e. the growth rates of the microalgae and cyanobacteria, may be very high. To give an order of magnitude, as put forward by some authors, a hectare of culture of microalgae can theoretically produce between 60 and 300 barrels of oil equivalent per year, versus 7 barrels with colza. To allow growth of microalgae or cyanobacteria, it is necessary to combine a strain with the appropriate culture medium. The latter is made up of water, nutrients, carbon dioxide ($CO_2$) and solar energy. Determination of these various parameters will give the rate of multiplication and accumulation of the algal biomass as well as its composition. Thus, for example, nitrogen deficiency in the culture medium may lead to an accumulation of lipids in the cells.

The three species of photosynthetic microorganisms currently the most cultivated are, in order of decreasing amount, the cyanobacteria of the genus *Arthrospira* better known by the designation "*Spirulina*", which represents about 50% of global production, followed by the green microalgae of the genera *Chlorella, Dunaliella, Haematococcus, Nannochloropsis* and the diatoms of the genus *Odontella*.

In general, apart from some species cultivated for niche markets, the methods of culture of the photosynthetic microorganisms have not yet reached their stage of industrial maturity. There are still problems with constancy of quality and the cost of production, which limits their access to many commercial markets. Moreover, production of photosynthetic microorganisms requires light as well as heat during cold periods. Now, so that it is not limited to just the hot and sunny regions, the technical solutions adopted must allow the productivity of the microalgae to be increased in countries located at the latitudes of the temperate regions.

There are a great many systems for monoculture production of photosynthetic microorganisms in suspension in water.

There are two main classes of culture systems [1] for photosynthetic microorganisms (algal biomass):

- systems with an architecture of the open type, which consist of basins, if applicable in a loop, also known as "raceway culture systems", lagoons, outdoor tanks, i.e. in the open air. Their main advantage is that the resultant production costs are relatively low. Their major drawbacks are low volume productivity, i.e. large size of equipment required for a given production of biomass, and poor control of the culture conditions (notably sensitivity to impurities),
- systems with an architecture of the closed type, known as "photo-bioreactors", consisting of one or more enclosure(s), i.e. whose interior is not in contact with the ambient air. Although requiring a large initial investment, photo-bioreactors make it possible, compared to the open systems, to achieve better productivity and carry out culture in conditions that are better controlled, notably avoiding impurities, contaminants, and losses of $CO_2$.

Hydrothermal liquefaction is a promising method of conversion for transforming algal biomass into so-called third generation biofuels. It is a process operating with subcritical water, i.e. in conditions of temperature and pressure below 374° C. and 22.1 MPa, in which water plays a dual role of reaction medium and reagent. To a first approximation, this process makes it possible to transform an algal biomass, still in solution in its culture medium, into a biocrude, much closer to a liquid fuel.

However, a major drawback of this method of conversion by hydrothermal liquefaction is the production of an aqueous effluent during the reaction. This contains the nutrients necessary for growth of the algae, but also carbon compounds, some of which are toxic to the algae.

Thus, at the laboratory scale, plenty of people have already demonstrated the feasibility of conversion of algal biomass by hydrothermal liquefaction.

In particular, the applicant has already shown that hydrothermal liquefaction is a conceivable method for converting numerous algae (*Nannochloropsis, Chlorella, Neochloris, Spirulina, Chlamydomonas, Dunaliella*, etc.), still in their culture medium, into a combustible biocrude.

Publication [2] presents investigations of different temperatures and residence times of the algal biomass in a reactor for carrying out hydrothermal liquefaction. This publication [2] shows that short residence times, typically from 1 to 5 minutes, are sufficient to obtain high degrees of conversion into biocrude, of up to 66%, and values of gross calorific value (GCV) up to 36 MJ/kg. Recycling of the effluents from the process is not considered in this publication [2].

Publication [3] is interested in the hydrothermal liquefaction of aqueous wastes, and of an algal biomass. In this publication [3], recycling of the nutrients and carbon from the culture medium of the algae is envisaged: the recycling scheme envisaged is shown in FIG. 1 in the publication. In this publication [3], the residue from hydrothermal liquefaction does not, however, undergo further treatment, but is used directly for cultivating algae, and this may prove harmful and non-optimal for the culture, as certain compounds resulting from hydrothermal liquefaction are toxic.

More generally, the various teams working on hydrothermal liquefaction are publishing similar, very encouraging results, in terms of degrees of conversion into biocrude, and calorific value of the biocrude obtained.

In other words, the feasibility of transforming an algal biomass, or even of agricultural and food wastes, into biocrude has now been demonstrated, and the level of the performance attainable by a continuous process of hydrothermal liquefaction is understood.

Patent application US 2012/0055077 proposes an improvement of the method of hydrothermal liquefaction of biomass by post-treatment of the biocrude obtained from hydrothermal liquefaction to improve its properties as biofuel. This patent application does not concern itself with the reprocessing of the aqueous phase obtained from liquefaction.

Patent application WO 2011/049572 proposes a method of hydrothermal liquefaction of a waste, and of utilizing the $CO_2$ obtained for culturing algae, the algal biomass thus obtained being in its turn converted by hydrothermal liquefaction. In the method disclosed, there is very little upgrading of the aqueous phase obtained from hydrothermal liquefaction. In fact, it is simply reinjected directly into the culture medium for the algae, and this may prove toxic for the algae and not optimal for their growth.

Patent application US 2012/0285077 proposes a biological type of extraction of the lipids contained in algae in order to obtain a bio-oil, which is then converted into biodiesel by carrying out a transesterification reaction. The method disclosed in this application envisages recycling of the residues by fermentation to form $CO_2$, which is then reinjected into a reactor for algal culture.

Thus, although there are many teams working on the development of the method for converting algal biomass into biocrude by hydrothermal liquefaction, and although this method involves considerable production of aqueous effluents during the reaction, no solution has really been proposed for making the best possible use of these aqueous effluents.

There is a need to improve the methods for thermochemical conversion of algal biomass into gas or into biocrude with a view to producing biofuels (liquid or gaseous), notably with a view to making the best possible use of the aqueous effluents produced in these processes.

More generally, there is a need to improve the continuous processes that integrate a method for thermochemical conversion of algal biomass into gas or into biocrude downstream of a method for culture of algal biomass.

The general aim of the invention is to meet this need or these needs at least partly.

SUMMARY OF THE INVENTION

For this purpose, the invention firstly relates, according to one aspect, to a method for converting algal biomass, i.e. the set of photosynthetic microorganisms, into a gas or into a biocrude with a view to producing a fuel or a motor fuel, notably a liquid fuel, or some other synthetic product, comprising the following steps:

a/ hydrothermal gasification or hydrothermal liquefaction of an algal biomass in at least one first reactor, b/ separation between respectively the gas or the biocrude produced, and the aqueous effluents and the $CO_2$ produced, at the outlet of the first reactor, c/ recovery of the aqueous effluents, d/ oxidation of the aqueous effluents in at least one second reactor.

step d/ being a wet-process oxidation or hydrothermal oxidation (HTO) in supercritical conditions.

Thus, the invention makes it possible firstly both to produce gas or biocrude and to transform the harmful aqueous effluents efficiently in order to recycle them. The aqueous effluents thus transformed no longer constitute waste products.

More precisely, at the outlet of the first reactor, a gas or biocrude can be recovered that is directly usable for producing liquid fuels, and at the outlet of the second reactor, it is possible to recover and utilize water and nutrients as well as the $CO_2$ produced during hydrothermal gasification or liquefaction.

According to another of its aspects, the invention also relates to a continuous process for culture of algal biomass and conversion of the algal biomass cultivated into a gas or into a biocrude, comprising the following steps:

culturing, in a culture zone containing a culture medium, the algal biomass to be cultivated, harvesting the algal biomass cultivated, steps a/ to d/ of the conversion process described above, injecting the water and the nutrients, and if applicable the $CO_2$, obtained at the outlet of the second reactor, into the culture zone.

According to an advantageous embodiment, the continuous process further comprises the step of recovery of the oxygen ($O_2$) produced by the algal biomass, to inject it, as oxidant, upstream of the second reactor before the oxidation step d/.

Thus, the invention proposes integrating recycling of the effluents produced, actually within the continuous process, by employing two reactors, one dedicated to hydrothermal gasification or liquefaction for upgrading the algal biomass into fuel and the other dedicated to oxidation of the aqueous effluents to allow them to be recycled to the culture medium of the algal biomass.

When the two reactors are coupled thermally, the energy released by the exothermic oxidation reaction can be utilized to the best possible degree, by supplying it as a heat source to the endothermic reaction of hydrothermal gasification or liquefaction.

Thus, the invention offers many advantages, including:

a saving on the reprocessing of the $CO_2$ and aqueous effluents at the outlet of the process for converting the algal biomass into gas or into biocrude, these aqueous effluents no longer constituting waste products that have to be reprocessed, as in the prior art.

recovery of a nontoxic culture medium (water and nutrients at the outlet of the oxidation reactor) for culture of the algal biomass, and therefore a production saving for culturing it, supply of energy for the endothermic reaction of hydrothermal liquefaction from the exothermic oxidation reaction.

When step a/ is a liquefaction, it is preferably carried out in the temperature range between 150 and 374° C. and/or pressures between 0.5 and 35 MPa.

When step a/ is a gasification, it is preferably carried out in a temperature range between 374 and 800° C. and/or pressures between 22.1 and 35 MPa.

Preferably, step a/ is carried out in a range of residence time between 15 seconds and 1 hour.

When step d/ is an oxidation by a wet process it is carried out in a temperature range between 150 and 374° C. and/or pressures between 0.5 and 35 MPa.

When step d/ is a hydrothermal oxidation it is carried out in a temperature range between 374 and 800° C. and/or pressures between 22.1 and 35 MPa.

Step d/ is preferably carried out in a range of residence time in the second reactor between 15 seconds and 1 hour.

According to an advantageous embodiment, step d/ is an oxidation by a wet process carried out with a part of the biocrude produced injected into the second reactor.

The $CO_2$ produced and separated may be injected, as solvent, into the biocrude produced.

According to an advantageous embodiment, the heat produced during step d/of oxidation in the second reactor may be supplied to the first reactor for carrying out step a/ of hydrothermal liquefaction or gasification.

The heat produced during step d/ of oxidation in the second reactor may also be supplied for preheating the oxidizing gas.

According to an advantageous embodiment, step a/ of hydrothermal liquefaction and step d/ of oxidation are carried out in one and the same reactor, called a double-jacketed reactor, comprising an inner jacket delimiting the chamber of the first reactor internally, and an outer jacket surrounding the inner jacket, the space between the inner jacket and the outer jacket defining the chamber of the second reactor.

Advantageously, step a/ of hydrothermal liquefaction or gasification is carried out in several first reactors fluidically in parallel.

Also advantageously, step d/ of oxidation is carried out in several second reactors fluidically in parallel.

The invention also relates to a continuous process for culture of algal biomass and conversion of the algal biomass cultivated into a gas or into a biocrude, comprising the following steps:

culture of the algal biomass in a zone containing a culture medium harvesting the algal biomass cultivated, steps a/ to d/ of the method of conversion as claimed in one of the preceding claims, injecting the water and the nutrients, and if applicable the $CO_2$, obtained at the outlet of the second reactor, into the culture zone.

The method may further comprise the step of recovery of the oxygen ($O_2$) produced by the algal biomass, to inject it, as oxidant, upstream of the second reactor before the oxidation step d/.

The invention also relates to the use of the method of conversion described above or the continuous process described above for producing so-called third-generation liquid fuels.

DETAILED DESCRIPTION

Other advantages and features of the invention will become clearer on reading the detailed description of the invention given for purposes of illustration and nonlimiting, referring to the following figures, where:

FIG. 3 is a schematic view of an example of a system using a continuous process for culture of algal biomass and conversion of the algal biomass cultivated by hydrothermal liquefaction into biocrude according to the state of the art;

FIG. 4 is a schematic view of an example of a system using a continuous process according to the invention and applied directly to the system according to FIG. 3;

In the description given hereunder, the terms "inlet", "outlet" "upstream" and "downstream" are used by reference to the direction of circulation of the products obtained within the system employing the continuous process according to the invention.

The notation X wt % signifies a percentage X by weight of a compound.

Figure 1:
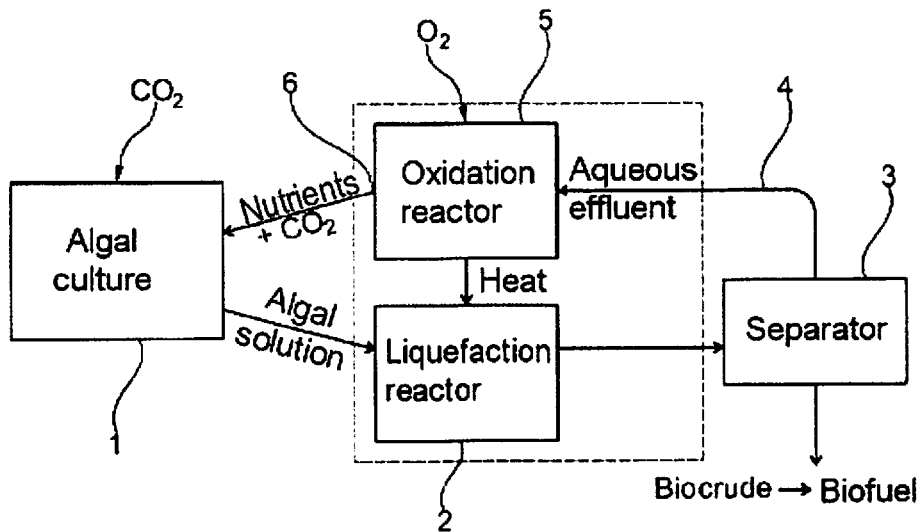
FIG. 1 is a schematic view of an example of a system employing the continuous process for culture of algal biomass and conversion of the algal biomass cultivated by hydrothermal liquefaction into biocrude according to the invention.

FIG. 1 shows schematically a first example of a system employing the continuous process for culture of photosynthetic microorganisms and conversion thereof by hydrothermal liquefaction according to the present invention.

The system comprises firstly a zone 1 for culture of the algal biomass. This culture zone is either in the open air, with one or more basins, or of the closed type, with one or more photo-bioreactors (PBR).

The open-air basin may be of the type with a loop or loops, usually called "raceway".

For culture of the following species of microalgae and cyanobacteria, the following preferred temperature ranges may be envisaged:

*Arthrospira platensis:* 25-35° C. (optimal temperature=30° C.),

*Chlorella pyrenoidosa:* 35-45° C. (optimal temperature=38.7° C.),

*Chlorella vulgaris:* 25-35° C. (optimal temperature=30° C.),

*Chlamydomonas reinhardtii:* 15-30° C. (optimal temperature=25° C.),

*Phaeodactylum tricornutum:* 20-25° C. (optimal temperature=22.5° C.),

*Porphyridium cruentum:* 15-30° C. (optimal temperature=19.1° C.),

*Scenedesmus sp.:* 20-33° C. (optimal temperature=26.3° C.),

*Nannochloropsis oceanica:* 20-33° C. (optimal temperature=26.7° C.),

*Dunaliella tertiolecta:* 30-39° C. (optimal temperature=32.6° C.).

The algal biomass obtained by culture is then harvested.

Various techniques may be used for harvesting, such as flocculation, filtration, centrifugation.

The subsequent step of hydrothermal liquefaction offers the advantage of operation with a high moisture level, up to 80 wt % of water, or even more. In contrast to other conversion technologies, this makes it possible to simplify the steps of harvesting and drying.

The harvested biomass may be sent, notably by means of a suction pump 10, to a reactor 2 for transforming the algal biomass into biocrude (oily phase) by hydrothermal liquefaction. Besides the biocrude at reactor outlet 2, there is formation of an aqueous phase, containing organic residues and nutrients of the culture medium, and a gas phase, containing primarily $CO_2$. In other words, the reaction of hydrothermal liquefaction, which is endothermic, allows the transformation of an algal solution, partially concentrated in its culture medium, into biocrude of interest, an aqueous effluent, and $CO_2$. The biocrude obtained may then undergo a post-treatment, of hydro-liquefaction for example, to be transformed into biofuel of the biodiesel type.

According to the invention, at the outlet of reactor 2, separation is performed between the aqueous effluents, $CO_2$, and the biocrude by means of a suitable device 3, which may be a usual device.

Then the aqueous effluents, preferably with the $CO_2$, are sent via a return line to the inlet of a reactor 5, in which a wet-process oxidation reaction will take place.

The oxidation reaction, which is an exothermic reaction, allows the aqueous effluents obtained by the liquefaction reaction in reactor 1 to be transformed into water containing the nutrients present in the initial algal solution, and into $CO_2$. For it to take place, this reaction requires an oxidant, which may be air, oxygen, or some other. For the wet-process oxidation reaction to be viable energetically, it is preferable that the separation of the phases at the outlet of liquefaction take place without cooling or depressurizing the mixture.

Then, at reactor outlet, a mixture of nutrients with water and optionally $CO_2$ is obtained, which may be injected via line 6 into the culture zone 1. This mixture is therefore recyclable to the algal culture.

Thus, according to the invention, the aqueous effluents are treated by oxidation at the outlet of hydrothermal liquefaction, for fresh algae to be cultured.

Moreover, the invention described allows the best possible energy utilization.

In fact, the reaction of liquefaction requires heating of the algal solution and is endothermic, whereas the oxidation reaction is exothermic.

Thus, as shown schematically in FIG. 1, the heat derived from the exothermic wet-process oxidation reaction that takes place in reactor 5 is supplied to reactor 2 for carrying out or participating in the hydrothermal liquefaction.

Figure 2:
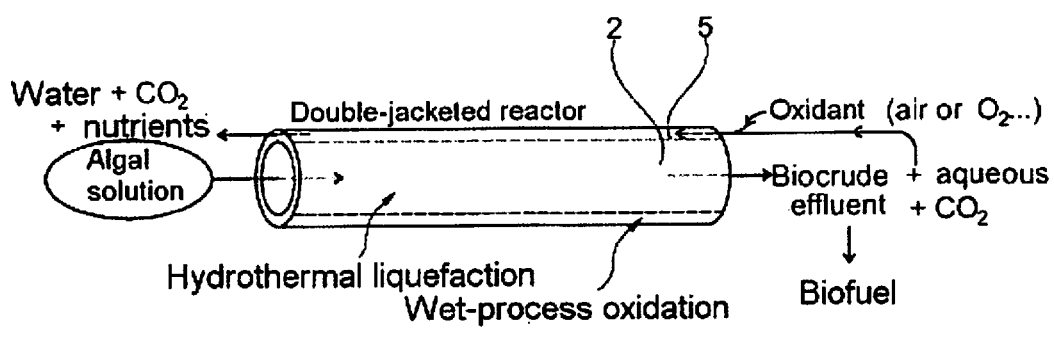
FIG. 2 is a perspective schematic view of an advantageous embodiment of a part of the system according to the invention with a double-jacketed reactor.

Thus, to combine these two reactions, a so-called double-jacketed reactor 7 as illustrated in FIG. 2 may be used advantageously. In this reactor 7, the inner jacket delimits the chamber of reactor 2 in which the reaction of hydrothermal liquefaction takes place and the space between the inner jacket and the outer jacket delimits the chamber of reactor 5 in which the wet-process oxidation reaction takes place (or vice versa).

The structure and operation of said double-jacketed reactor 7 will now be explained.

Reactor 7 is tubular and its length gives a sufficient contact surface between the two reaction zones, and thus improves the heat exchange.

Moreover, a small diameter makes it possible to minimize the thickness required for containing the internal pressure. The outer jacket must withstand the mechanical stresses: pressure and temperature, and the chemical stresses connected with oxidation of organic matter and the ions derived from the mineral salts. Typically, the outer jacket of reactor 7 may be made of steel 316L or Inconel 625®. If necessary, to improve the chemical durability of the reactor, titanium lining may be envisaged.

The inner jacket is used with equal pressure between the two reaction zones, therefore it does not have to withstand pressure. It must, however, withstand the thermal stresses, provide good thermal conductivity, and withstand the chemical stresses of the two reactions, i.e. both of liquefaction in chamber 2 and of oxidation in chamber 5. Typically, an inner jacket of titanium may be envisaged, which can withstand chemical and thermal stresses, but it has a lower thermal conductivity. Steel 316L or Inconel 625® may also be used.

Instead of using a double-jacketed reactor 7, it is also possible to the use other heat exchanger systems (tubular exchangers, tube-bundle exchangers, spiral-tube exchangers, etc.), or else utilize the energy produced by the oxidation reaction in some other way.

FIG. 3 shows a system using a method with continuous conversion of algal biomass culture and conversion of the cultivated algal biomass by hydrothermal liquefaction into biocrude according to the state of the art.

In a system of this kind, the aqueous effluents and the $CO_2$ produced are troublesome wastes.

To overcome this drawback, the inventors thus proposed the method described above with optimized recycling:
  by oxidation of the aqueous effluents recovered at the outlet of the separating device 3,
  and then by injecting a stream consisting of water, $CO_2$ and nutrients produced by oxidation in culture zone 1.

For performing the wet-process oxidation reaction it is necessary to add an oxidant to the mixture. This may be air, oxygen, hydrogen peroxide, or some other. Advantageously, it is possible to recover the $O_2$ produced during growth of the algae in the culture zone and inject it before the step of wet-process oxidation, i.e. at reactor inlet 5 as indicated in FIG. 4.

Thus, according to the invention, the coproducts of the reaction of hydrothermal liquefaction, which are troublesome in the system according to the state of the art, are actually utilized in the method of culture of the algal biomass.

With the additional oxidation step according to the invention, the energy efficiency of the hydrothermal liquefaction process is increased, and reprocessing and utilization of the troublesome effluents at process outlet become possible.

The preferred parameters and conditions for carrying out the various steps of the method according to the invention are presented below.

Hydrothermal Liquefaction Step i. Products at Inlet

At the inlet of reactor 2, various types of algae may be injected (*Nannochloropsis, Chlorella, Neochloris, Spirulina, Chlamydomonas, Dunaliella,* etc.), at varying concentration in their culture medium.

For performing a liquefaction test, the algal solution advantageously has a concentration between 10 wt % and 40 wt % of dry matter (organic and inorganic matter), knowing that the elemental chemical composition of the dry matter is within the following ranges of values:
- 20 to 70 wt % of carbon
- 5 to 40 wt % of oxygen
- 5 to 10 wt % of hydrogen
- 5 to 10 wt % of nitrogen
- 3 to 50 wt % of inorganic salts (compounds of P, K, Cl, Na, S, Mg, Ca, Fe, Al, F, etc.).

Hereafter, an intermediate concentration of 20 wt % of dry matter is considered, made up as follows: 55 wt % of carbon, 25 wt % of oxygen, 7 wt % of hydrogen, 8 wt % of nitrogen and 5 wt % of salts. This composition ($C_{6.0}H_{9.1}O_{2.0}N_{0.7}$) corresponds to a gross calorific value (GCV) of the dry matter of about 24.5 MJ/kg.

ii. Operating Conditions

The reaction temperature is in the range 200 to 350° C. for pressures varying between 5 and 25 MPa.

Figure 5:
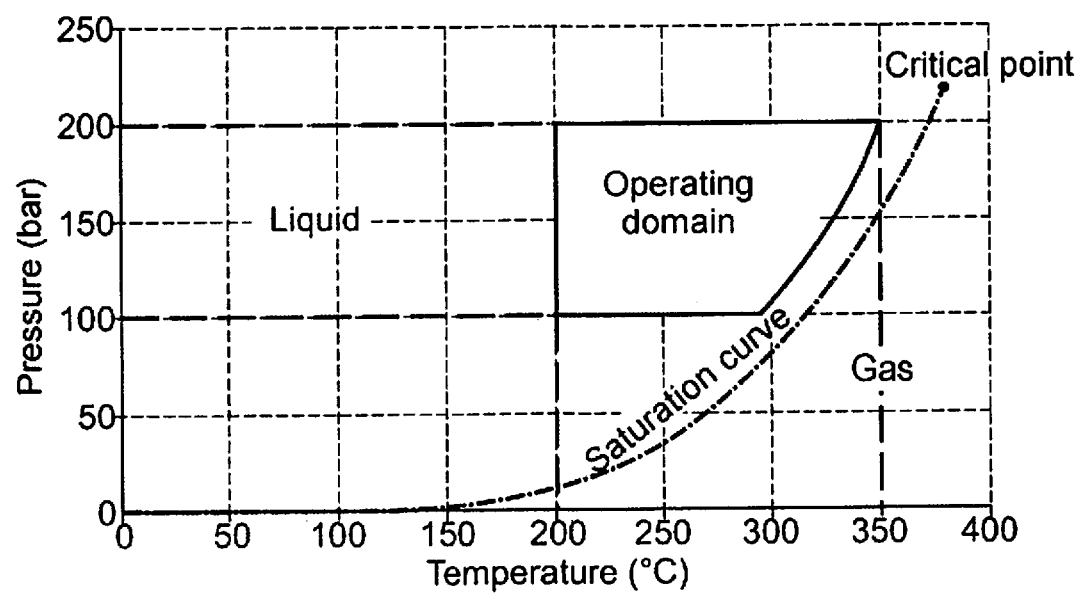
FIG. 5 is a graph indicating the preferred ranges of temperature and pressure for carrying out step a/ of hydrothermal liquefaction in the method according to the invention.

Typically, for the liquefaction reaction to take place, the temperature and pressure conditions must be in the operating domain in FIG. 5.

The pressure/temperature pair must be maintained in such a way that the medium is not in the phase gas.

The residence time in these conditions may be within a range from 1 to 60 minutes.

Hereafter, a test at 290° C., and 10 MPa, with a residence time of 5 minutes, is considered. It goes without saying that this is only one example among the multitudes of possible operating conditions.

Treatment of one kilogram of algal solution, with density equal to 1 to a first approximation, requires about 1000 kJ to heat the water present in the algal solution from 20 to 290° C., and about 125 kJ to heat the organic and inorganic matter.

This constitutes a first approximation of the energy to be supplied ideally for heating the reaction mixture. The enthalpy of the liquefaction reaction is to be added to this value. According to the estimates in publication [4], this can be estimated at 27 kJ in these conditions.

The operating conditions may have a considerable effect on the results.

Thus, the temperature, pressure, residence time, type and strain of algae, their concentrations, and their methods of culture, will cause the level of biocrude obtained and its quality to vary, as well as the nature of the aqueous effluent and its concentration of carbon compounds.

iii. Products at Outlet

In the conditions stated above, we expect approximately 7 wt % of biocrude (with a gross calorific value close to 32 to 38 MJ/kg), 1 wt % of $CO_2$, supercritical in these conditions of temperature and pressure, and 92 wt % of aqueous effluent.

The latter contains 6 wt % of organic carbon, or 54.8 g of carbon per liter of algal solution treated.

Wet-Process Oxidation Step

When a double-jacketed reactor 7 is used, this wet-process oxidation reaction takes place in the space between the inner and outer jackets (or conversely in the internal zone).

iv. Products at Inlet

The aqueous effluents resulting from the liquefaction reaction, as well as an oxidant such as air or oxygen, are introduced at the inlet of reactor 5.

The aqueous phase, containing carbon compounds and $CO_2$, thus undergoes wet-process oxidation in these conditions of temperature and pressure, through addition of an oxidant.

To a first approximation, the 54.8 g of carbon present in the aqueous effluents can release 1800 kJ during oxidation (according to the elemental composition of the carbon compounds, the value will in reality be between 1000 and 1800 kJ).

To a first approximation, this value is therefore sufficient to supply the necessary energy, as heat for the reaction of hydrothermal liquefaction and for heating of the oxidant.

v. Operating Conditions

The wet-process oxidation reaction takes place in the same conditions as hydrothermal liquefaction, i.e. in a temperature range from 200 to 350° C., and a range of pressure between 5 and 25 MPa. The oxidant must be added in an amount above stoichiometric (1.5 for example).

The residence time required is thus of the order of 1 to 60 minutes.

For 54.8 g of carbon we require a theoretical minimum of 146.1 g of oxygen to ensure complete theoretical oxidation.

In reality, above-stoichiometric is favorable. For example, for 1.5 above stoichiometric, 219.2 g of oxygen is required.

Since the oxygen arrives at room temperature, 54.5 kJ is required to heat it to the reaction temperature. If the oxidant is air, 767.6 g of nitrogen would be added, requiring 213.3 kJ for heating from 20 to 290° C.

vi. Products at Outlet

At the outlet of the oxidation reactor 5, the stream is composed of a favorable medium for culture of algae, containing water, $CO_2$ and the nutrients initially present in the algal solution.

These elements may be injected into the culture zone directly.

Other variants and improvements may be envisaged while remaining within the scope of the invention.

The invention is not limited to the examples that have just been described; it is notably possible for characteristics of the examples illustrated in variants that are not illustrated to be combined together.

The expression "comprising a" (or "comprising one") must be understood as being a synonym of "comprising at least one", unless stated otherwise.

REFERENCES CITED

[1]: J. Pruvost et al. "*Industrial production of microalgae and cyanobacteria*", Techniques de l'ingénieur, Ind, 200, 11/2011.

[2]: Julia L. Faeth, et al.: "*Fast Hydrothermal Liquefaction of Nannochloropsis sp. to Produce Biocrude*", Energy Fuels, 2013, 27 (3), pp 1391-1398.

[3]: Yan Zhou, et al.: "*A synergistic combination of algal wastewater treatment and hydrothermal biofuel production maximized by nutrient and carbon recycling*", Energy & Environmental Sciences, 2013, 6, 3765-3779.

[4]: Mariane Audo: "*Evaluation of the rheological potential of oils derived from microalgae for applications as bitumen substitutes*" Doctorate Thesis, 2013, Nantes University, doctoral school 3MPL.

The invention claimed is:

1. A method for converting algal biomass into a gas or biocrude with a view to producing a fuel, a motor fuel, or a liquid fuel, or some other synthetic product, comprising:
    (a) gasification or hydrothermal liquefaction of an algal biomass in at least one first reactor;
    (b) separation between respectively the gas or biocrude produced and the aqueous effluents and the $CO_2$ produced at the outlet of the first reactor;
    (c) recovery of the aqueous effluents; and (d) oxidation of the aqueous effluents in at least one second reactor;

wherein step (d) is oxidation by a wet process or a hydrothermal oxidation (HTO) in supercritical conditions.

2. The method of conversion according to claim 1, wherein step (a) is a liquefaction process carried out at a temperature ranging from 150° C. to 374° C.

3. The method of conversion according to claim 1, wherein step (a) is a liquefaction process carried out at a pressure ranging from 0.5 MPa to 35 MPa.

4. The method of conversion according to claim 1, wherein step (a) is a gasification process carried out at a temperature ranging from 374° C. to 800° C.

5. The method of conversion according to claim 1, wherein step (a) is a gasification process carried out at a pressure ranging from 22.1 MPa to 35 MPa.

6. The method of conversion according to claim 1, wherein step (a) is carried out for a residence time ranging from 15 seconds to 1 hour.

7. The method of conversion according to claim 1, wherein step (d) is a wet-process oxidation carried out at a temperature ranging from 150° C. to 374° C.

8. The method of conversion according to claim 1, wherein step (d) is a wet-process oxidation carried out at a pressure ranging from 0.5 MPa to 35 MPa.

9. The method of conversion according to claim 1, wherein step (d) is a hydrothermal oxidation carried out at a temperature ranging from 374° C. to 800° C.

10. The method of conversion according to claim 1, wherein step (d) is a hydrothermal oxidation carried out at a pressure ranging from 22.1 MPa to 35 MPa.

11. The method of conversion according to claim 1, wherein step (d) is carried out for a residence time in the second reactor ranging from 15 seconds to 1 hour.

12. The method of conversion according to claim 1, wherein step (d) is a wet-process oxidation carried out with part of the biocrude produced injected into the second reactor.

13. The method of conversion according to claim 1, wherein the $CO_2$ produced is further separated and injected, as solvent, in the biocrude product.

14. The method of conversion according to claim 1, wherein the heat produced during step (d) of oxidation in the second reactor is supplied to the first reactor for carrying out step (a) of hydrothermal liquefaction or gasification.

15. The method of conversion according to claim 1, wherein the heat produced during step (d) of oxidation in the second reactor is supplied for preheating an oxidizing gas.

16. The method of conversion according to claim 1, wherein step (a) of hydrothermal liquefaction and step (d) of oxidation are carried out in a double-jacket reactor, said double-jacket reactor comprising an inner jacket delimiting the chamber of the first reactor internally, and an outer jacket surrounding the inner jacket, with the space between the inner jacket and the outer jacket defining the chamber of the second reactor.

17. The method of conversion according to claim 1, wherein step (a) of hydrothermal liquefaction or gasification is carried out in several first reactors fluidically in parallel.

18. The method of conversion according to claim 1, wherein step (d) of oxidation is carried out in several second reactors fluidically in parallel.

19. A continuous process for culture of algal biomass and conversion of the algal biomass cultivated into a gas or into a biocrude, comprising:

(a') culturing the algal biomass in a zone containing a culture medium;

(a") harvesting the cultivated algal biomass;

(a) gasification or hydrothermal liquefaction of an algal biomass in at least one first reactor;

(b) separation between respectively the gas or biocrude produced and the aqueous effluents and the $CO_2$ produced at the outlet of the first reactor;

(c) recovery of the aqueous effluents;

(d) oxidation of the aqueous effluents in at least one second reactor; and (d') injecting the water, nutrients, and any $CO_2$ obtained at the outlet of the second reactor, into the culture zone.

20. The continuous process according to claim 19, further comprising (d") recovery of any oxygen ($O_2$) produced by the algal biomass to inject it, as oxidant, upstream of the second reactor before the oxidation step (d).

* * * * *